United States Patent [19]

Stoerr

[11] Patent Number: 4,531,297
[45] Date of Patent: Jul. 30, 1985

[54] MEASUREMENT METHOD AND DEVICE FOR FACILITATING THE MOUNTING OF CORRECTIVE GLASSES ON A SPECTACLE FRAME

[75] Inventor: Jacques Stoerr, San Francisco, Calif.

[73] Assignee: Essilor International (Compagnie Generale d'Optique), Creteil, France

[21] Appl. No.: 545,927

[22] Filed: Oct. 27, 1983

[30] Foreign Application Priority Data

Nov. 3, 1982 [FR] France .................................. 82 18385

[51] Int. Cl.³ .............................................. A61B 3/10
[52] U.S. Cl. ........................................ 33/200; 33/507; 351/204
[58] Field of Search ................. 33/200, 174 D, 174 A; 351/200, 204, 218

[56] References Cited

U.S. PATENT DOCUMENTS

| | | | |
|---|---|---|---|
| 1,675,407 | 7/1928 | Dvorine | 33/200 |
| 2,632,257 | 3/1953 | Belgard | 33/200 |
| 2,677,894 | 5/1954 | Belgard | 351/204 |
| 3,987,554 | 10/1976 | Pastore | 33/200 |
| 4,208,800 | 6/1980 | Grolman et al. | 33/200 |

*Primary Examiner*—Willis Little
*Attorney, Agent, or Firm*—Burgess, Ryan & Wayne

[57] ABSTRACT

A measurement device for the mounting of corrective glasses on a spectacle frame. The device has a transparent support for plate 4, the upper part 6 of which is opaque and is provided with a slot 5 acting as an origin for horizontal graduations 4a which are used for the measurement. The device is used for the determination of the height H separating the center of the pupil of the eye from the lowest part 3 of the interior of the spectacle frame circle 2.

9 Claims, 2 Drawing Figures

MEASUREMENT METHOD AND DEVICE FOR FACILITATING THE MOUNTING OF CORRECTIVE GLASSES ON A SPECTACLE FRAME

BACKGROUND OF THE INVENTION

The present invention concerns a measurement device for the mounting of corrective glasses on a spectacle frame, and especially corrective glasses having progressively variable focal power.

The device according to the present invention allows, on the one hand, to measure the distance separating the center of each pupil of a patient's eye from the point that is situated on the lower, internal edge of the corresponding circle of the frame and that is vertically the furthest from the center of the pupil and, on the other hand, to verify the compatibility of the frame with the prescribed corrective glasses. A device adapted to fulfill this function has already been proposed, especially in French Pat. No. 77 07641, in the name of the applicant (French publication No. 2,384,232).

However, the device described in this patent is destined to be placed in the rim groove of one of the circles of a spectacle frame and cannot be used in combination with a clip frame or a frame of which the upper or lower part of the circles comprises by a flexible thread, for example, a nylon thread.

Furthermore, this device is difficult to use with frames, of which the lowest parts of the circles are very eccentric and situated on the side of the temples of the spectacle wearer.

Other measurement devices for use in combination with any type of frame exist, such as described in U.S. Pat. No. 1,675,407. These devices comprise by a graduated scale disposed on a transparent plate. It has been shown from experience that these devices are not sufficiently precise, since it is difficult to carry out an exact reading while checking that the patient indeed observes the distant point or object that has been designated; and these devices conception and the manner of utilization resluting therefrom, are the give rise to measurement errors due essentially to a lack of parallax.

One of the aims of the present invention is to overcome the disadvantages of such prior art measurement devices and to enable the practitioner to carry out a rapid measurement that is both objective and subjective and, consequently, to obtain high precision with respect to the real needs of a spectacle user.

Furthermore, the device according to the invention enables measurement of the horizontal distance separating the center of each pupil from the internal edge of the corresponding circle situated on the temporal side and the furthest from the pupil.

SUMMARY OF THE INVENTION

With this in mind, the measurement device for mounting corrective glasses on a spectacle frame, especially progressively variable focal power glasses, is to allow designed (i) the verification of the compatibility of these glasses with the frame and with the spectacle frame wearer, and (ii) the monocular measurement of the vertical position of the center of the pupils of the eyes of the wearer with respect to the lower internal edge of the circles of the frame. The device comprises a transparent plate adapted to be placed before the eyes of a patient and provided with a graduated scale and a positioning mark, the center of which constitutes the original reference of the graduation scale. According to the invention the upper part of the transparent plate is in the form of a blade and is opaque; and the positioning marker comprises a transparent zone in the form of a slot, disposed transversely along the length of the blade. This slot is adapted to be maintained in a substantially horizontal position for the measurement.

According to an embodiment of the invention, the opaque part situated below the horizontal slot in usage position of the plate presents a predetermined height that corresponds to the minimal height for mounting a predetermined type of corrective glass, this minimal height being in practice between 18 and 24 mm. The height of the slot on this opaque part is, preferably, substantially equal to 1 millimeter.

According to the invention, for objective utilization of the device the patient equipped with the frame is made to observe an object substantially situated at the level of his eyes. Then the opaque part of the transparent plate is placed opposite the eye of the patient on the frame to be checked, and this plate is displaced until the luminous image line of the slot observed on the patient's eye coincides with the center of the pupil of this eye, and on the graduated scale the value of the vertical distance separating the center of the pupil from the lowest internal part of the corresponding frame circle is read. The position of the opaque zone of the transparent plate with respect to this lowest part of the internal frame circle indicates whether the frame is or is not compatible with the prescribed glasses, and thus whether or not that the patient has a sufficiently comfortable vision.

For subjective utilization of the measurement device that the patient equipped with the frame is made to observe an object situated substantially at the level of his eyes, then the opaque part of the transparent plate is placed opposite the eye of the patient on the frame to be controlled, the plate being held by the patient or the practitioner, and this opaque part is displaced before the eye of the patient so that the patient sees the object center between the edges of the slot. The value of the vertical distance separating the center of the slot from the lowest internal part of the corresponding circle of the frame is then read on the graduated scale. The position of the opaque zone of the transparent plate with respect to this lowest part of the internal circle of the frame indicates whether or not the frame is compatible with the prescribed glasses, and thus whether or not the patient a sufficient vision comfort.

BRIEF DESCRIPTION OF THE DRAWINGS

Other aims, advantages and characteristics of the invention will appear from reading through the description of the embodiment of the invention and its process of utilization, given by way of non-limitative example and with respect to the annexed drawings in which.

DESCRIPTION OF THE PREFERRED EMBODIMENT

Figure 1:
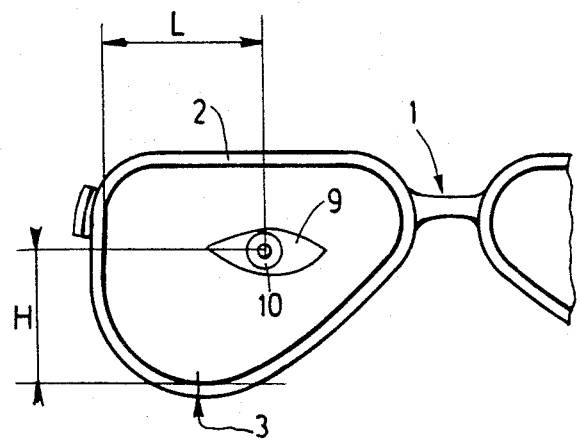
FIG. 1 schematically represents a cut-away front view of a circle of a spectacle frame, the lowest part of which is eccentric and situated on the side of the patient's temples.

According to FIG. 1 in which is represented a spectacle frame 1 that presents a circle 2 the lowest part of which in utilisation position, is indicated by arrow 3, it is necessary to verify, on the one hand, that the distance H separating the center of the pupil of the patient's eye from zone 3 will be sufficient to ensure the patient a normal vision comfort and to measure, on the other hand, this distance H for the mounting of the corrective glasses.

Figure 2:
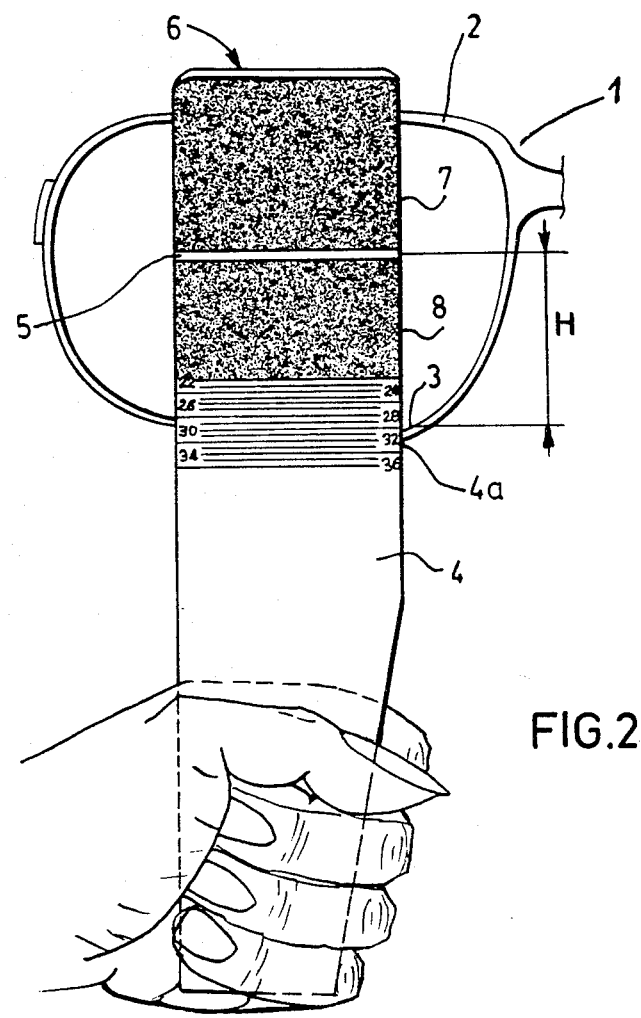
FIG. 2 represents the transparent measurement plate disposed opposite the circle of a spectacle frame worn by a patient.

The measurement equipment according to the invention and represented in FIG. 2 allows this measurement in an objective manner and, which is very important, also in a subjective manner, according to the vision habits of the patient.

The measurement device according to the invention is constituted by a transparent plate 4 on which is engraved a graduated scale 4a, on either side of the transparent slot 5 provided on an opaque part 6 of the transparent plate. The graduations 4a thus take their origin from the center of this slot that preferably has a height of about one millimeter.

These graduations can be read on the transparent part of the plate where they begin to appear at a distance from the slot 5 corresponding to the minimum height of mounting of the prescribed glass, a height which is in practice between 18 and 24 mm, extending to about 40 millimeters corresponding substantially to the maximum radius of the corrective glasses presently available.

The opaque part 6 of the transparent plate 4 is divided in FIG. 2 by slot 5 (which need not extend along the total length of plate 4) into an upper part 7 that is not used for the measurement of dimensions and a lower part 8 that immediately indicates to the operator whether this frame suits or does not suit the chosen glasses and will or will not be comfortable for its wearer.

In order to proceed with measurement by using the device according to the invention, the patient puts the spectacles frame to be tried in position on his face and looks at a distant luminous point.

When the opaque part 6 of the plate 4 is placed by the operator, before one of the eyes of the patient, the transparent horizontal slot 5 provides two functions. On the one hand, when this slot is suitably placed opposite the patient's pupil, it allows the patient to observe the object which has been designated to him. On the other hand, by reason of the opaque zone surrounding the slot 5, the slot creates a luminous horizontal image line that the operator can observe on the eye 9 of the patient and can check even if the luminous line passes through the center of the pupil 10 of this eye (see FIG. 1).

According to a first embodiment corresponding to an objective measurement, the practitioner or operator that observes by the side the eye of the patient, places the plate 4 so that the slot 5 is too high or too low, the patient not being able in this case to see the distant point that is designated to him. Of course, the other eye can be hidden by an opaque mask so as not to trouble the patient.

The practitioner thereafter displaces the support 4 vertically until the luminous line that he observes on the eye of the patient coincides with the center of the pupil 10 of this eye. He can thus read on the graduated scale 4a the value of the distance H measured vertically separating the center of the pupil 10 from the point 3 of the lowest internal part of the corresponding frame circle 2. Since the practitioner simply has to cause a luminous image to coincide with an object no parallax error is introduced by the process and the device according to the invention, whereas all the known devices can cause a measurement error due to parallax. If the lowest part 3 is not visible to the practitioner and is hidden by opaque zone 8 situated under the horizontal slot 5, the frame is not compatible with the prescribed glasses.

According to a second embodiment corresponding to a subjective measurement, the practitioner who vertically displaces before eye 9 of the patient the opaque part 6 comprising the horizontal slot 5, requests the patient to indicate the moment when he sees the object that is shown to him centered between the two edges of the slot. At this instant, the practitioner can read on the scale 4a the value of the vertical distance H to be determined.

For further security, the practitioner can combine the two objective and subjective utilization processes of the device according to the invention.

The object that the patient is asked to look at and which is substantially situated at the level of his eyes, can be a distant object, a luminous or other point, or an object brought nearer to the patient, such as the image of the patient's own face produced by a mirror.

Of course, the present invention is not limited to the embodiments and utilization process described and represented and it is adaptable to numerous variants available to the man skilled in the art, without departing from the spirit and scope of the invention.

The device according to the invention can be used for measuring the distance L (FIG. 1) separating the center of the pupil from the internal edge of the frame spectacle situated on the temporal side and which is the furthest from the pupil. In this case, slot 5 will, of course, be vertically disposed.

According to another variation, the opaque part 6 can be replaced by a transparent zone, and the slot 5 can be replaced by an opaque line at the same level. The image of the slot on the eye is thus a dark line.

What is claimed is:

1. A measurement device for mounting corrective glasses on a spectacle frame to verify the compatability of the lenses of said glasses with the frame and with the spectacle wearer and for the monocular measurement of the vertical position of the centers of the pupils of the eyes of the wearer with respect to the lower internal edge of the frame circles, said device comprising a transparent plate adaped to be placed before the eyes of a patient and provided with a graduated scale and a positioning marker, the center of said marker comprising the original reference of the graduated scale, the upper part of the transparent plate being in the shape of a blade and being opaque, the positioning marker comprising a transparent zone in the form of a slot disposed transversely across the blade in the opaque upper part of the transparent plate, said slot being adapted to be maintained in a substantially horizontal position during a measurement.

2. A device according to claim 1, wherein the opaque part situated below the horizontal slot in the usage position of the plate presents a predetermined height that corresponds to the minimal height of the mounting of prescribed glasses between 18 and 24 mm.

3. A device according to claim 1 or 2, wherein the height of the slot provided the opaque part of the plate is about 1 millimeter.

4. An objective measurement process for facilitating the mounting of corrective glasses on a spectacle frame, comprising the steps of:
   providing a transparent plate having a graduated scale and a positioning marker, the center of said marker being the origin reference of the graduated scale, the upper part of the transparent plate having the shape of a blade and being opaque, the positioning marker comprising a transparent zone in the form of a slot disposed transversely across the blade in the opaque upper part of the transparent plate, said slot being maintained in a substantially horizontal position during a measurement;
   causing a patient equipped with the frame to observe an object situated substantially at the level of his eyes;
   placing the opaque part of the transparent plate opposite the eye of the patient on the frame to be checked;
   displacing the plate until the luminous image line of the slot observed on the patient's eye coincides with the center of the pupil of the eye; and
   reading the vertical distance separating the center of the pupil from the lowest part of the frame circle on the graduated scale, the position of the opaque zone of the transparent plate with respect to the lowest part of the internal frame circle indicating whether the frame is compatible with the prescribed glasses.

5. An objective measurement process for the measurement device for facilitating the mounting of corrective glasses on a spectacle frame, comprising the steps of:
   providing a transparent plate having a graduated scale and a positioning marker, the center of said marker being of the origin reference of the graduated scale, the upper part of the transparent plate having the shape of a blade and being opaque, the positioning marker comprising a transparent zone in the form of a slot disposed transversely across the blade in the opaque upper part of the transparent plate, said slot being maintained in a substantially horizontal position during a measurement;
   causing a patient equipped with the frame to observe an object situated substantially at the level of his eyes;
   placing the opaque part of the transparent plate opposite the eye of the patient on the frame to be checked;
   displacing the plate until the patient can see the object centered between the edges of the slot; and
   reading the value of the vertical distance separating the center of the slot from the lowest internal part of the corresponding frame circle on the graduated scale, the position of the opaque zone of the transparent plate with respect to the lowest part of the internal frame circle indicating whether the frame is compatible with the prescribed glasses.

6. An objective measurement process for facilitating the mounting of corrective glasses on a spectacle frame, comprising the steps of:
   providing a transparent plate having a graduated scale and a positioning marker, the center of said marker being of the origin reference of the graduated scale, the upper part of the transparent plate having the shape of a blade and being opaque, the positioning marker comprising a transparent zone in the form of a slot disposed transversely across the blade in the opaque upper part of the transparent plate, said slot being maintained in a substantially horizontal position during a measurement, the opaque part situated below the horizontal slot in the usage position of the plate having a height that corresponds to the minimal height of the mounting of prescribed glasses between 18 and 24 mm;
   causing a patient equipped with the frame to observe an object situated substantially at the level of his eyes;
   placing the opaque part of the transparent plate opposite the eye of the patient on the frame to be checked;
   displacing the plate until the luminous image line of the slot observed on the patient's eye coincides with the center of the pupil of the eye; and reading the vertical distance separating the center of the pupil from the lowest part of the frame circle on the graduated scale, the position of the opaque zone of the transparent plate with respect to the lowest part of the internal frame circle indicating whether the frame is compatible with the prescribed glasses.

7. A subjective measurement process for the measurement device for facilitating the mounting of corrective glasses on a spectacle frame, comprising the steps of:
   providing a transparent plate having a graduated scale and a positioning marker, the center of said marker being the origin reference of the graduated scale, the upper part of the transparent plate having the shape of a blade and being opaque, the positioning marker comprising a transparent zone in the form of a slot disposed transversely across the blade in the opaque upper part of the transparent plate, said slot being maintained in a substantially horizontal position during a measurement, the opaque part situated below the horizontal slot in the usage position of the plate having a height that corresponds to the minimal height of the mounting of prescribed glasses between 18 and 24 mm;
   causing a patient equipped with the frame to observe an object situated substantially at the level of his eyes;
   placing the opaque part of the transparent plate opposite the eye of the patient on the frame to be checked;
   displacing the plate until the patient can see the object centered between the edges of the slot; and
   reading the vertical distance separating the center of the slot from the lowest internal part of the corresponding frame circle on the graduated scale, the position of the opaque zone of the transparent plate with respect to the lowest part of the internal frame circle indicating whether the frame is compatible with the prescribed glasses.

8. An objective measured process for the measurement device for facilitating the mounting of corrective glasses on a spectacle frame, comprising the steps of:
   providing a transparent plate having a graduated scale and a positioning marker, the center of said marker being the origin reference of the graduated scale, the upper part of the transparent plate having the shape of a blade and being opaque, the positioning marker comprising a transparent zone in the form of a slot disposed transversely across the blade in the opaque upper part of the transparent plate, said slot being maintained in a substantially horizontal position during a measurement, the height of the slot provided on the opaque part of the plate being about 1 millimeter;

causing a patient equipped with the frame to observe an object situated substantially at the level of his eyes;

placing the opaque part of the transparent plate opposite the eye of the patient on the frame to be checked;

displacing the plates until the luminous image line of the slot observed on the patient's eye coincides with the center of the pupil of the eye; and reading the vertical distance separating the center of the pupil from the lowest part of the frame circle on the graduated scale, the position of the opaque zone of the transparent plate with respect to the lowest part of the internal frame circle indicating whether the frame is compatible with the prescribed glasses.

9. A subjective measurement process for the measurement device for facilitating the mounting of corrective glasses on a spectacle frame, comprising the steps of:

providing a transparent plate having a graduated scale and a positioning marker, the center of said marker being the origin reference of the graduated scale, the upper part of the transparent plate having the shape of a blade and being opaque, the positioning marker comprising a transparent zone in the form of a slot disposed transversely across the blade in the opaque upper part of the transparent plate, said slot being maintained in a substantially horizontal position during a measurement, the height of the slot provided on the opaque part of the plate being about 1 millimeter, causing a patient equipped with the frame to observe an object situated substantially at the level of his eyes;

placing the opaque part of the transparent plate opposite the eye of the patient on the frame to be checked;

displacing the plate until the patient can see the object centered between the edges of the slot; and reading the vertical distance separating the center of the slot from the lowest internal part of the corresponding frame circle on the graduated scale, the position of the opaque zone of the transparent plate with respect to the lowest part of the internal frame circle indicating whether the frame is compatible with the prescribed glasses.

* * * * *